(12) United States Patent
Hinden et al.

(10) Patent No.: US 9,526,881 B2
(45) Date of Patent: Dec. 27, 2016

(54) INSECT BITE ITCH STOPPER

(75) Inventors: Joseph Gavigan Hinden, Glen Head, NY (US); Benjamin Ward Huser, Boston, MA (US); Garret Kane Daffemer, New York, NY (US)

(73) Assignee: X Tech, LLC, Brooklyn, NY (US)

(*) Notice: Subject to any disclaimer, the term of this patent is extended or adjusted under 35 U.S.C. 154(b) by 876 days.

(21) Appl. No.: 13/530,316

(22) Filed: Jun. 22, 2012

(65) Prior Publication Data
US 2013/0345648 A1 Dec. 26, 2013

(51) Int. Cl.
*A61M 35/00* (2006.01)
*A61B 19/00* (2006.01)

(52) U.S. Cl.
CPC .................. *A61M 35/003* (2013.01)

(58) Field of Classification Search
CPC .............. A61M 35/00; A61B 19/00
See application file for complete search history.

(56) References Cited

U.S. PATENT DOCUMENTS

| | | | |
|---|---|---|---|
| 3,900,018 A * | 8/1975 | Piunno | A61B 17/00 128/897 |
| 6,386,778 B1 * | 5/2002 | Guay et al. | 401/45 |
| 2005/0054991 A1 * | 3/2005 | Tobyn | B65D 83/0011 604/290 |
| 2008/0214984 A1 * | 9/2008 | Caracci | A61F 6/12 604/12 |
| 2011/0245784 A1 * | 10/2011 | Johnson | A61K 9/0014 604/290 |
| 2012/0283668 A1 * | 11/2012 | Shalev | A45D 34/04 604/290 |

* cited by examiner

*Primary Examiner* — Philip R Wiest
*Assistant Examiner* — Sara Sass
(74) *Attorney, Agent, or Firm* — The McHattie Law Firm, LLC; Clay D. Shorrock, Esq.

(57) ABSTRACT

An insect-bite itch stopper is disclosed which has a pressure surface adapted for pressing directly onto an insect bite and an applicator for simultaneously or contemporaneously applying an anti-itch medication to the bite.

4 Claims, 6 Drawing Sheets

//: # 
INSECT BITE ITCH STOPPER

CROSS REFERENCE TO RELATED APPLICATIONS

[N/A]

STATEMENT REGARDING FEDERALLY SPONSORED RESEARCH OR DEVELOPMENT

[N/A]

NAMES OF PARTIES TO JOINT RESEARCH AGREEMENTS

[N/A]

REFERENCE TO "SEQUENCE LISTING," TABLE, OR COMPUTER PROGRAM LISTING APPENDIX SUBMITTED ON COMPACT DISC/INCORPORATION-BY-REFERENCE OF MATERIAL ON COMPACT DISC

[N/A]

FIELD OF THE INVENTION

The present invention relates to a device and method for providing relief for insect bites and stings.

BACKGROUND OF THE INVENTION

Spending time outdoors inevitably exposes people to the painful and itchy bites or stings of mosquitoes, gnats, chiggers, wasps, bees and other biting insects and pests (hereafter "insect bites.") Generally, biting insects pierce the victim's skin with elongated mouth parts and inject their saliva to aid in the consumption of the victim's blood. The itching and irritation associated with insect bites is caused both by the structural damage caused by the bite as well as the victim's immune response to the insect's saliva.

Multiple strategies have been employed to address the unpleasant after effects of insect bites. There are both physical and pharmacological treatment options available that are aimed at soothing the itching and stinging associated with insect bites. One commonly used treatment for insect bites is to press one's fingernail into the bite, creating an "X" shape directly at the situs of the bite. This is a purely mechanical treatment that is thought to be effective by creating uneven pressure within the bite and thereby distributing the insect's saliva into a larger volume of tissue, thereby lessening its irritant effects. Similarly, prior art teaches a device for applying a crescent-cross configured pressure surface to a insect bite thereby effectuating itch relief. For example, a hand-held device with 2 intersecting arcuate fins that define an upstanding crescent cross adapted for pressing directly into an insect bite and creating unbalanced pressure within the bite thereby dispersing the irritant and stopping the itching associated with the bite.

In addition to purely mechanical treatments, a variety of topical pharmacological treatments are available to relieve the pain and itching associated with insect bites. Some topical treatments that have had success include, either alone or in combination, baking soda, ammonia, tea tree oil, rubbing alcohol, soap, vinegar, honey, underarm deodorant, bleach, tea, meat tenderizer, salt water, epsom salts, crushed antacid tablets, aspirin, various lotions, topical steroids, topical antihistamines, topical anesthetics, fruit juices, poultices of leaves, and other natural or pharmacological formulations.

One application device that has gained prominence as a preferred means of topical treatment delivery is the elongated pen-like applicator. These applicators, well known to those skilled in the art, generally comprise a means for storing the liquid to be applied, and an applicator surface that serves to transfer the liquid from the storage means to the skin of the user. The pen-like applicator has been successful because it allows for easy application of a liquid to the user's skin with minimal mess or need for other equipment such as cotton swabs.

While both the mechanical treatments and the pharmacological treatments have proven effective at reducing the itching and stinging associated with insect bites there is no device or method described in the prior art that teaches a combination of mechanical and pharmacological treatments for insect bites. It is therefore the object of the present invention to provide a insect bite itch stopper that combines a mechanical treatment for insect bites with the application of a pharmacologically active formulation with known itch stopping properties.

SUMMARY OF THE INVENTION

The insect bite itch stopper of the present invention comprises a pressure surface for applying uneven pressure at the situs of the insect bite and an applicator for simultaneously or contemporaneously applying a pharmacologically active anti-itch compound to the affected area.

In order to effectuate the application of uneven pressure to the situs of the bite, the invention contemplates the use of 2 blades disposed normally to each other such that they define an upstanding crescent-cross adapted to be pressed against the skin of the user at the situs of the bite. The blades come together such that they define 4 spaces interspersed with the blades, sufficient to house an applicator or operative part thereof. The invention also contemplates other configurations for the pressure surface such as a square grid, a triangular grid or other conformation suitable for pressing into an insect bite and creating uneven pressures within the bite.

In a first embodiment, the pressure surface and the applicator are static relative to one another. The pressure surface may extend slightly past the edge of the applicator so that the pressure surface may be pressed into the affected skin before the applicator makes contact with the user. The invention is utilized by having the user press the pressure surface directly onto the insect bite which then causes the applicator to come into contact with the affected area and deliver to the affected area a pharmacologically effective amount of itch/sting relieving solution.

In another embodiment, the applicator is dynamically mounted relative to the pressure surface such that when the pressure surface is placed against the user's skin, the applicator does not come in contact with the user's skin until the user activates a mechanism that moves the applicator into contact with the user's skin.

In another embodiment, the pressure surface is dynamically mounted relative to the applicator such that when the applicator is placed onto the user's skin, the pressure surface does not come in contact with the user's skin until the user activates a mechanism that moves the pressure surface into contact with the user's skin.

These and other systems, methods, objects, features, and advantages of the present disclosure will be apparent to those skilled in the art from the following detailed description of the embodiments and drawings.

All documents mentioned herein are hereby incorporated in their entirety by reference. References to items in the singular should be understood to include items in the plural, and vise versa, unless explicitly stated otherwise or clear from the text. Grammatical conjunctions are intended to express any and all disjunctive and conjunctive combinations of conjoined clauses, sentences, words, and the like, unless otherwise stated or clear from context

DETAILED DESCRIPTION OF THE DRAWINGS

The following detailed description is of the best currently contemplated modes of practicing the invention. The description is not to be taken in a limiting sense, but is made merely for the purpose of illustrating the general principles of the invention since the scope of the invention is best defined by the appended claims.

Figure 1:
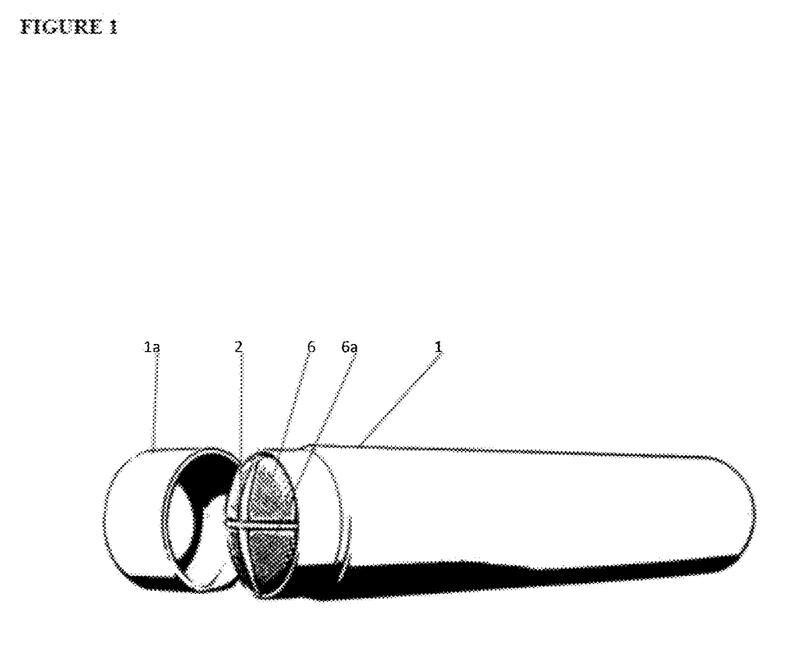
FIG. 1 shows an embodiment of the insect bite itch stopper that highlights the applicator and the pressure surface oriented about each other to form a compound surface.

The invention comprises a pressure surface (2) capable of creating uneven pressure within an insect bite and an applicator (6) capable of applying an effective amount of a suitable anti itch formulation to an insect bite. The pressure surface may be comprised of a plurality of intersecting blades or other suitable conformation. The applicator (6) may be comprised of any suitable applicator technology known to those skilled in the art. To function according to the invention, the applicator and the pressure surface are oriented about each other such that they form a compound surface where both the pressure surface and the applicator are exposed and capable of making contact with the affected area on a user contemporaneously (6a). A "Compound Surface" is one that is comprised of more than one functional or structural surface. For example a surface formed by the interpolation of an absorbent material and upstanding blades. "Contemporaneously" should be interpreted to include the possibility that the pressure surface and the applicator come in contact with the insect bite sequentially, during a single use, and that the pressure surface or applicator may be utilized alone according to user preference. The term "insect bite(s)" should be interpreted to also include other itchy skin lesions such as those caused by poison ivy, or other infections, or irritant agents.

Figure 2:
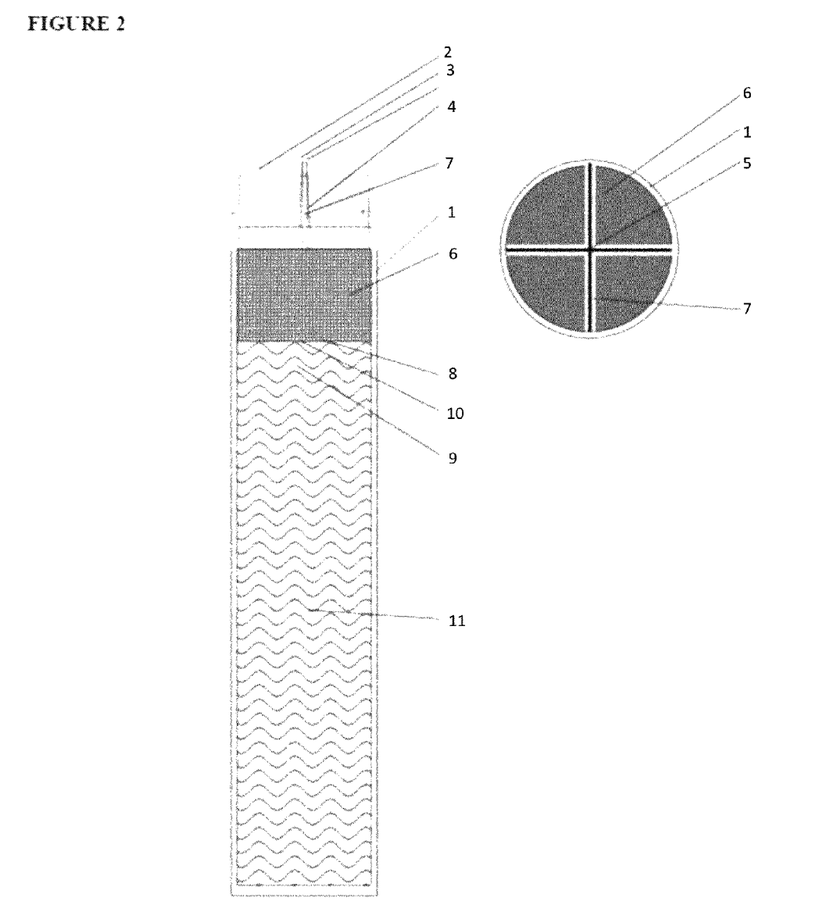
FIG. 2 shows an cut-away view of the insect bite itch stopper in an embodiment in which the pressure surface and applicator are fixed relative to one another.

In a preferred embodiment, the invention comprises a housing (1), a liquid storage reservoir holding an anti itch formulation (9), an applicator tip (6), an interface (8) disposed in between the liquid storage reservoir and the applicator tip, and a pressure surface (2) adapted to be pressed into the skin of the user at the situs of the insect bite. The liquid storage reservoir further comprises a front end (9a) and a back end (9b). The front end of the liquid storage reservoir may be perforated with one or more holes (10) to allow the liquid in the reservoir to escape. An interface may be positioned in contact with the front end of the liquid storage reservoir to allow the liquid to pass through in a controlled manner, but not allow the liquid to spill out. The interface may take the form of a valve, pressure sensitive diaphragm, semipermeable material or other configuration known to those skilled in the art. For example, U.S. Pat. No. 2,949,621 and patent application Ser. Nos. 10/368,841 and 10/914,144 describe liquid applicators with varying forms of interfaces designed to allow liquid to flow to an applicator tip. The liquid storage reservoir contains a liquid, gel or other suitable formulation (11) of an effective agent for treating the discomfort associated with insect bites. An applicator tip (6) is disposed in contact with the interface (8) such that it will absorb the liquid in the liquid storage reservoir (9) and transfer it onto the skin of the user when the applicator tip is pressed against the skin of the user. The applicator tip further comprises cut-outs (7) adapted to interpolate with the pressure surface (2) such that the blades of pressure surface are almost entirely encompassed and contained within the cutouts of the applicator (7) and project slightly above the surface of the applicator, forming a compound surface (6). The pressure surface (2) is comprised of a first, upstanding arcuate fin (3) mounted diametrically of the front end of the housing; a second arcuate fin (4) mounted diametrically of the front end of the housing (1) at 90 degrees to the first fin; the two fins intersecting at their midpoints (5) to define an upstanding crescent-cross (2) adapted to be pressed against the surface of an insect bite and create unbalanced pressures within the bite, thereby dispersing the irritant through a larger volume of tissue. A cap covering the applicator may be included with all embodiments (1a).

Figure 3:
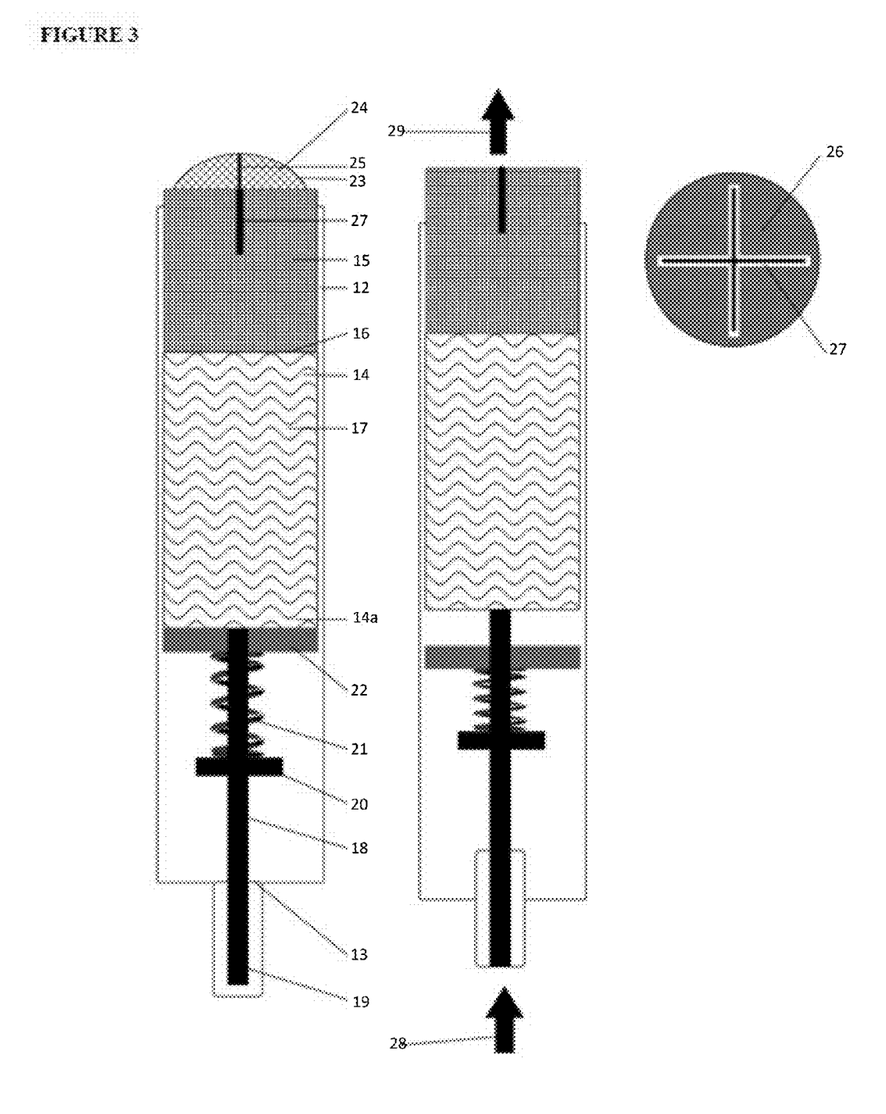
FIG. 3 shows an cut-away view of the insect bite itch stopper in which the applicator is dynamically mounted relative to the pressure surface.

In another preferred embodiment the invention comprises a housing (12) with a front end (12a) and a back end (12b) with an opening (13) that defines a hole in the back end of the housing (12). Fitting within the housing (12) there is a liquid storage reservoir (14) operatively connected to an applicator tip (15). An interface (16) may be disposed in between the liquid reservoir (14) and the applicator (15). The interface (16) may take the form of a valve, pressure sensitive diaphragm, semipermeable material or other configuration known to those skilled in the art. For example, U.S. Pat. No. 2,949,621 and patent application Ser. Nos. 10/368,841 and 10/914,144 describe liquid applicators with varying forms of interfaces designed to allow liquid to flow to an applicator tip. The liquid storage reservoir (14) contains a liquid, gel or other suitable formulation (17) of an effective agent for treating the discomfort associated with insect bites. An applicator tip (15) is disposed in contact with said interface (16) such that it will absorb the liquid in the liquid storage reservoir and transfer it onto the skin of the user when the applicator tip (15) is pressed against the skin of the user. A shaft (18), extending from the back end of the liquid storage reservoir (14a) extends through the housing (12) and terminates in a button (19) that extends through the opening (13) at the back end of the housing (12b) (hereafter "button shaft".) A spring stop (20) is fixed to the button shaft (18) in between the back end of the housing (12b) and the back end of the reservoir assembly (14a). A spring (21) is disposed around the button shaft (18) and engages the spring-stop on the button shaft (20) and another spring stop affixed to the inner wall of the housing (22) such that when pressure is applied to the back end of the button shaft (18) the spring (21) provides resilient back pressure. A pressure surface (23), adapted to be pressed into the user's skin at the situs of the insect bite is affixed to the front end of the housing (12a). The pressure surface (23) is further comprised of a first, upstanding arcuate fin (24) mounted diametrically of the front end of the housing (12a); a second arcuate fin (25) mounted diametrically of the front end of the housing (12a) at 90 degrees to the first fin; the two fins intersecting at their midpoints to define an upstanding crescent-cross (23) adapted to be pressed against the surface of an insect bite and create unbalanced pressures within the bite, thereby dispersing the irritant through a larger volume of tissue. The intersecting blades of the pressure surface (23) define 4 separate arc shaped openings (26). The applicator (15) is constructed with cut-outs (27) that correspond to the positions of the arcuate fins (24, 25) such that the applicator (15) has 4 separate aspects that fit through the openings (26) defined by the intersecting blades (24, 25). When a user engages the button shaft (28), the 4 separate aspects of the applicator tip (15) move through the spaces created by the intersecting blades (26) of the pressure surface (23) and project out the front of the housing (29). While the preferred embodiment described herein depicts an "x" shaped pressure surface, other configurations that apply suitable forces are also contemplated by the invention.)

Figure 4:
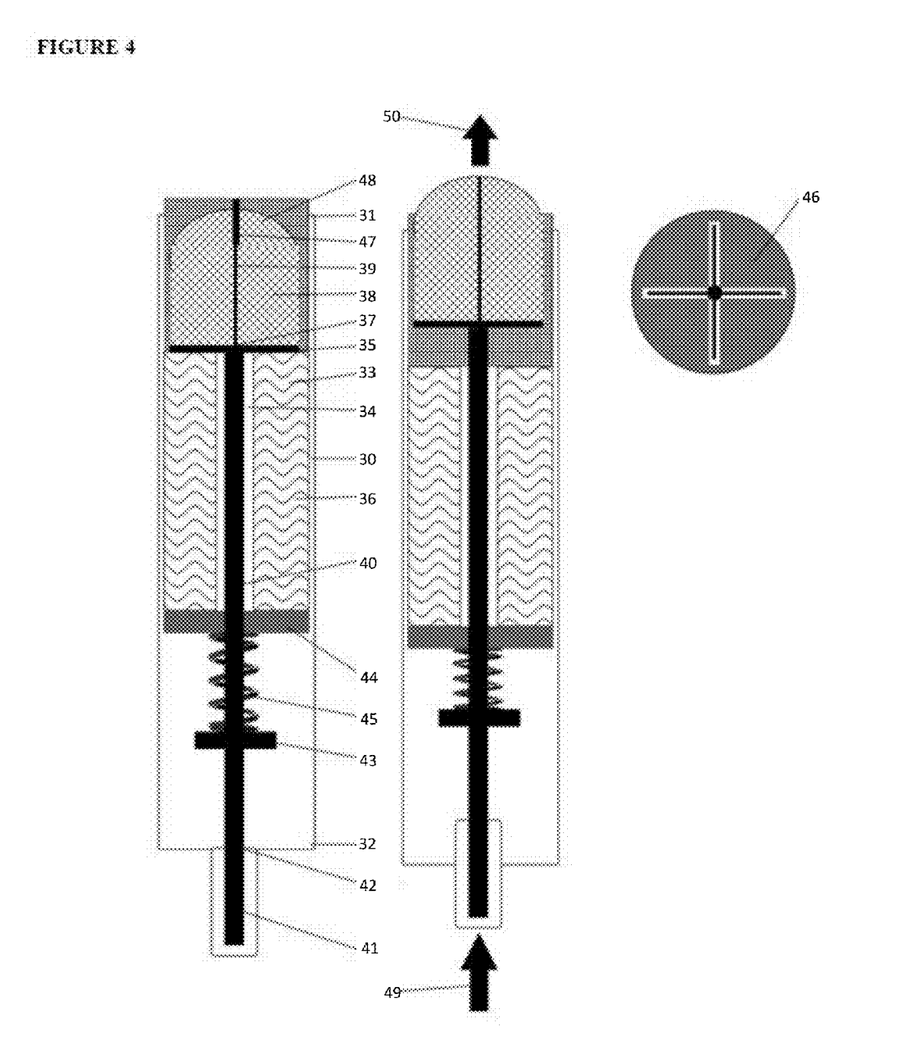
FIG. 4 shows an cut-away view of the insect bite itch stopper in which the pressure surface is dynamically mounted relative to the applicator.

In a third preferred embodiment, the invention comprises a housing (30) with a front end (31) and a back end (32) with an opening (42) that defines a hole in the back end (32). Fitting within the housing there is a liquid storage reservoir (33) operatively connected to an applicator tip (37a). The liquid storage reservoir (33) is constructed with a channel at its center which defines a tubular opening that runs the length of the liquid storage reservoir (34). An interface (35) may be disposed in between the liquid reservoir (34) and the applicator (37a). The interface (35) may take the form of a valve, pressure sensitive diaphragm, semipermeable material or other configuration known to those skilled in the art. For example, U.S. Pat. No. 2,949,621 and patent application Ser. Nos. 10/368,841 and 10/914,144 describe liquid applicators with varying forms of interfaces designed to allow liquid to flow to an applicator tip means. The liquid storage reservoir (33) contains a liquid, gel or other suitable formulation of an effective agent (36) for treating the discomfort associated with insect bites. An "X" shaped stamp (37) formed by the intersection of 2 arcuate blades (38, 39) disposed at a normal angle to each other is operatively connected to a shaft (40) that extends through the tubular opening (34) that runs the length of the liquid reservoir (33) and extends through the housing (30) and terminates in a button (41) that passes through the opening (42) at the back end of the housing (32) (hereafter "button shaft".) A spring stop (43) is fixed to the button shaft (43) in between the back end of the housing (32) and the back end of the liquid storage reservoir (33). A spring (45) is disposed around the button shaft (40) and engages the spring-stop on the button shaft (43) and another spring stop affixed to the inner wall of the housing (44) such that when pressure is applied to the back end of the button shaft (49) the spring provides resilient back pressure. The intersecting blades of the X-stamp (38, 39) define 4 separate arc shaped openings (46). The applicator (37a) is constructed with cut outs (47) that correspond to the positions of the arcuate blades (38, 39) of the x-stamp (37) such that the absorbent applicator has (37a) 4 separate aspects that fit through the openings defined by the intersecting blades of the X-stamp (37). At rest, the blades of the X-stamp are contained and encompassed within the cutouts (47) of the applicator (37a). When the user pushes the button (49) that extends out the back of the housing (32), the blades of the X-stamp (37, 38, 39) extend outwards (50) from the cut outs on the applicator (37a) and extend out of the housing (30).

Those skilled in the art would recognize many suitable materials for the applicator tip such as, but not limited to, polyester, cotton or other natural fibers, nylon fibers and the like. Appropriate applicator materials may also include "nibs" used in marking pens. Those skilled in the art would recognize many suitable materials for the pressure surface and x-stamp such as, but not limited to plastics, firm rubber, metals and the like.

Those skilled in the art would recognize that the pressure surface could take on a variety of confirmations including an x shaped stamp, a circular stamp, a plurality of intersecting blades and the like. Those skilled in the art would recognize that there are many different pharmacological formulations that would be effective in providing itch relief. The invention contemplates the use of the following, either alone or in combination as the pharmacologically active liquid to be applied to the insect bite: baking soda, ammonia, tea tree oil, rubbing alcohol, soap, vinegar, honey, underarm deodorant, bleach, tea, meat tenderizer, salt-water, epsom salts, crushed antacid tablets, aspirin, various lotions, topical steroids, topical antihistamines, topical anesthetics, fruit juices, poultices of leaves, and other natural or pharmacological formulations known to those skilled in the art. Those skilled in the art would also recognize that the housing described may take on various functional or ornamental shapes such as shapes ergonomically designed to fit within the hand of the user or shapes suggestive of an insect's body.

Figure 5:
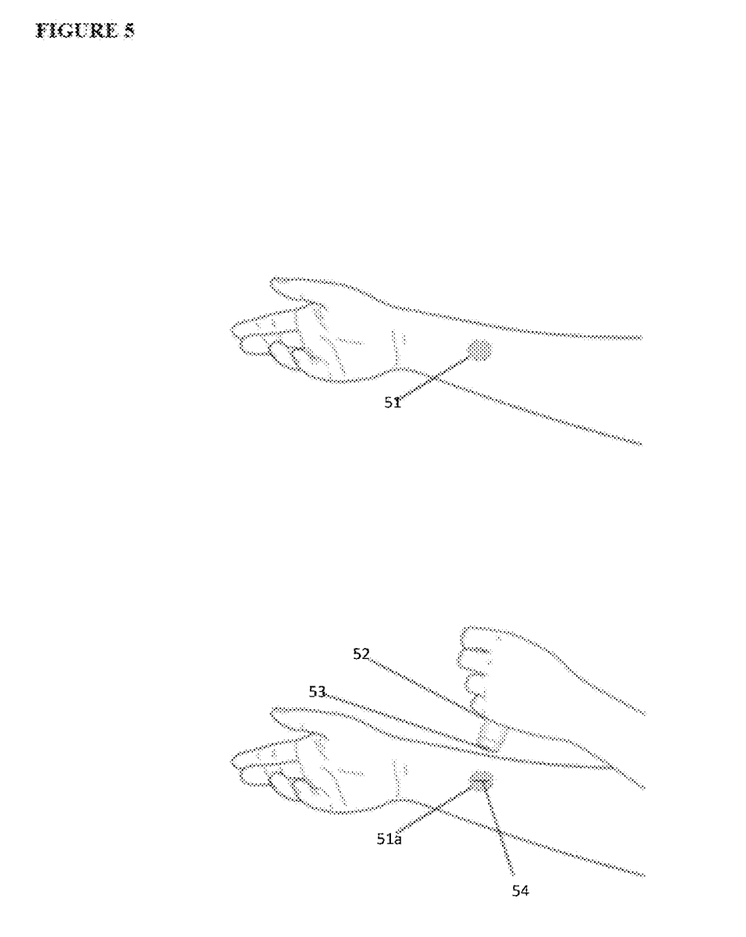
FIG. 5 shows the insect bite itch stopper in its static embodiment in use treating an insect bite.

In order to use the insect bite itch stopper the particular steps depend on which embodiment of the insect bite itch stopper is involved. For the embodiment of the itch stopper in which the applicator and the pressure surface are static, the device is used by performing the a single step of pressing the pressure surface (52) directly onto the skin of a user who has suffered an insect bite (51). Because the intersecting fins of the pressure surface are disposed within cut-outs of the applicator tip, the single step of pressing the pressure surface onto an insect bite also results in the applicator (53) coming in contact with the skin of the user (51) such that an effective amount of an anti-itch formulation is applied (54) to the insect bite (51) and the area immediately surrounding it (51a).

Figure 6:
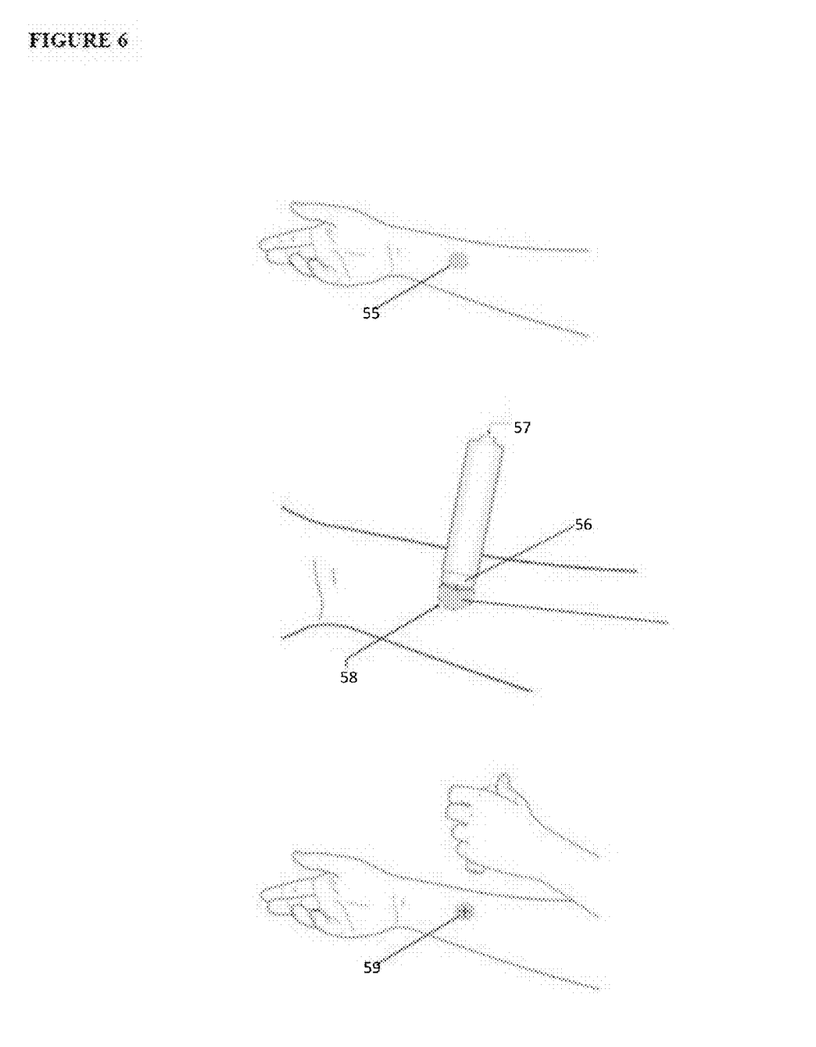
FIG. 6 shows the insect bite itch stopper in its dynamic embodiments in use treating an insect bite.

To use either of the embodiments in which the applicator and the pressure surface are movable relative to each other, the user positions the device such that the front end of the device (56) is pressed against the insect bite (55). Once in position, the user applies pressure to the back end of the button (57) shaft which moves either the pressure surface or the applicator tip, respectively, into contact with the insect bite (58). The device is then removed leaving behind an effective amount of anti itch formulation (59).

While the present disclosure includes many embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

We claim:

1. A device adapted to sequentially apply mechanical and pharmacological treatments to an insect bite comprising:
   a protruding pressure surface, said pressure surface comprising more than one empty space:

a liquid storage reservoir; and an absorbent applicator tip disposed below the protruding pressure surface in communication with the liquid reservoir;

said applicator tip further comprising cutouts adapted to allow the applicator tip to fully interpolate in the more than one empty spaces of the protruding pressure surface;

wherein the liquid storage reservoir contains an anti-itch formulation;

wherein the protruding pressure surface is comprised of two intersecting upstanding blades disposed perpendicularly to each other.

2. The device of claim 1 wherein the liquid storage reservoir contains an anti-itch formulation.

3. The device of claim 1 wherein the protruding pressure surface is comprised of two intersecting upstanding blades disposed perpendicularly to each other.

4. The device of claim 1 further comprising:

a housing with a front end and a back end;

a liquid storage reservoir with a front end and a back end within the housing, the liquid storage reservoir further comprising;

a permeable barrier on the front end of the liquid storage reservoir in communication with the absorbent applicator tip.

* * * * *